United States Patent [19]

Hider et al.

[11] Patent Number: 6,132,706

[45] Date of Patent: *Oct. 17, 2000

[54] METHODS OF MEDICAL TREATMENT FOR EXCESS PHOSPHATE USING GUANIDINO-CONTAINING POLYMERS

[75] Inventors: Robert Charles Hider, St. Osyth; Anthony Canas-Rodriguez, Canterbury, both of United Kingdom

[73] Assignee: BTG International Limited, London, United Kingdom

[*] Notice: This patent is subject to a terminal disclaimer.

[21] Appl. No.: 08/980,231

[22] Filed: Nov. 28, 1997

Related U.S. Application Data

[62] Division of application No. 08/491,855, Jul. 13, 1995, Pat. No. 5,698,190.

[30] Foreign Application Priority Data

Feb. 17, 1993 [GB] United Kingdom ................... 9303124
Apr. 23, 1993 [GB] United Kingdom ................... 9308408

[51] Int. Cl.[7] ................................................. A61K 31/74
[52] U.S. Cl. .................................. 424/78.08; 424/78.11; 424/78.12; 424/78.16; 424/78.35
[58] Field of Search ........................ 424/78.08, 78.11, 424/78.12, 78.16, 78.35

[56] References Cited

U.S. PATENT DOCUMENTS

| | | | |
|---|---|---|---|
| 2,945,006 | 7/1960 | Minsk et al. | 260/65 |
| 3,734,939 | 5/1973 | Schaefer | 260/404.5 |
| 4,071,459 | 1/1978 | Cohen et al. | 252/50 |
| 4,159,898 | 7/1979 | Cohen et al. | 44/63 |
| 4,478,984 | 10/1984 | Bryan | 525/333.6 |
| 5,496,545 | 3/1996 | Holmes-Farley et al. | 424/78.11 |
| 5,667,775 | 9/1997 | Holmes-Farley et al. | 424/78.11 |

FOREIGN PATENT DOCUMENTS

| | | |
|---|---|---|
| 1168210 | 12/1958 | France . |
| 2200457 | 7/1973 | Germany . |
| 62-230806 | 10/1987 | Japan . |
| 867 449 | 12/1958 | United Kingdom . |
| 850281 | 10/1960 | United Kingdom . |
| 857193 | 12/1960 | United Kingdom . |
| 1068543 | 5/1967 | United Kingdom . |
| 1374381 | 11/1974 | United Kingdom . |
| 1486603 | 9/1977 | United Kingdom . |
| WO 92/04385 | 3/1992 | WIPO . |

OTHER PUBLICATIONS

U.S. application No. 08/895,087, Hider et al., filed Jul. 15, 1997.
Patent Abstracts of Japan, vol. 12 No. 103 (C–485)(2950) Apr. 5, 1988, abstracting JP–A 62–230806.
Patent Abstracts of Japan, vol. 6 No. 4598 (C–77)(4598) 1977, abstracting JP–A 52–139050.
Patent Abstracts of Japan, vol. 9 No. 125 (C–283)(1848) May 30, 1985, abstracting JP–A 60–011509.
Patent Abstracts of Japan, vol. 4 No. 119 (C–22)(601), Aug. 23, 1980, abstracting JP–A 55–073706.
Derwent Japan Patent Abstract WPI Accession No. 85–053864/09 abstracting JP–A 60–011509, 1985.
Derwent Japan Patent Abstract WPI Accession No. 80–684066/39, abstracting JP–A 55–104357, 1980.
Derwent Japan Patent Abstract WPI Accession No. 80–33546C/19, abstracting JP–A 55–042506, 1980.
Derwent Japan Patent Abstract WPI Accession No. 80–26758C/15, abstracting SU–A 615087, 1980.
A. Akelah and D.C. Sherrington, "Application of Functionalized Polymers in Organic Synthesis" Chem. Rev. 81, 557–587 (1981).
E. Batres and M.L. Hallensleben, "Poly(amidine)s and Poly(guanidine)s—Synthesis and Some Properties", Polymer Bulletin 1, 715–722(1979).
Chemical Abstracts 85, No. 144224d(1976) abstracting SU–A 523,112.
Y. Yamamoto and S. Kojima, Chapter 10 "Synthesis and Chemistry of Guanidine Derivatives" in S. Patai and Z. Rappoport (eds.), "The Chemistry of Amidines and Imidates", John Wiley & Sons Ltd., pp. 485–526 (1991).
P.Haddad and P.E. Jackson, "Ion Chromatography: principles and applications", Journal of Chromatography Library 46, 48–52 (1990).
Burt et al., "Ion–Exchange Resins as Potential Phosphate–Binding Agents for Renal Failure Patients: Effect of the Physicochemical Properties of Resins on Phosphate and Bile Salt Binding", Journal of Pharmaceutical Science 76, No. 5, 379–383 (1987).
McGary et al., "Polycation as an Alternative Osmotic Agent and Phosphate Binder in Peritoneal Dialysis", Uremia Investigation 8(2), 79–84 (1984–85).
J.A. Delmez and E. Slatopolsky, "Hyperphosphatemia: Its Consequences and Treatment in Patients with Chronic Renal Disease", American Journal of Kidney Diseases XIX, No. 4, 303–317 (1992).
G. Semenza, "Chromatographie von Polyelektrolyten V. Aminoäthyl–Cellulose und Guanidinoäthyl–Cellulose", Helv. Chim. Acta 43, 1057–1068 (1960), with partial translation.

*Primary Examiner*—Bernard Lipman
*Attorney, Agent, or Firm*—Nixon & Vanderhye

[57] ABSTRACT

The invention provides a physiologically acceptable polymer comprising a backbone to which are attached guanidino groups, the polymer having a minimum molecular weight of 10,000. The invention also extends to foodstuffs and pharmaceutical compositions comprising the physiologically acceptable polymer. Such foodstuffs and compositions are of value in controlling phosphate levels in the body.

21 Claims, No Drawings

METHODS OF MEDICAL TREATMENT FOR EXCESS PHOSPHATE USING GUANIDINO-CONTAINING POLYMERS

This is a divisional of application Ser. No. 08/491,855, filed Jul. 13, 1995, now U.S. Pat. No. 5,698,190.

BACKGROUND OF THE INVENTION

This invention relates to polymers containing guanidino groups which are capable of specifically binding to phosphate.

Kidney disorders are extremely common and may, if treatment is inappropriate or delayed, progress through to end stage renal conditions, the patient subsequently requiring dialysis treatment. Kidney dialysis patients suffer from elevated serum levels of phosphate. In addition, patients who possess inefficient Kidneys frequently develop "kidney stones" consisting of the two extremely insoluble salts, calcium phosphate and calcium oxalate. Both of these anions induce severe toxic effects in such patients. The development of elevated phosphate levels is minimised in these patients by the addition of aluminium hydroxide, magnesium hydroxide or calcium hydroxide or mixtures of any of these compounds in the diet. However the use of magnesium or calcium hydroxide can lead to acute side effects, hence aluminium hydroxide is the compound which is more commonly used. The presence of aluminium ions in the patient's intestine reduces the uptake of phosphate from the diet, thus decreasing the concentration of phosphate in the lumen. The result is a concentration gradient of phosphate from a high level in the blood to a low level in the lumen. Phosphate thus moves out of the blood down this concentration gradient and into the lumen. The continued treatment with aluminium hydroxide or related preparations leads to the gradual accumulation of aluminium ions in body tissues which then have to be removed by the administration of the compound desferrioxamine. Desferrioxamine, an iron-chelator, is known to have side effects, especially in people who are not "iron-overloaded" (for example as a result of blood transfusions). Kidney patients are not iron-overloaded, hence constant use of the compound desferrioxamine to reduce aluminium levels may lead to undesirable side effects.

DESCRIPTION OF THE INVENTION

It is therefore an object of the present invention to provide a more convenient way of reducing the uptake of phosphate from the diet in kidney patients and reducing phosphate levels in the blood of kidney patients.

It has been found that this may be achieved through the incorporation into a pharmaceutical composition or a foodstuff of a polymer comprising a backbone and guanidino groups attached to the said backbone. Phosphate ions are known to bind to guanidino groups. This attraction is very strong, involving two electrostatic bonds and two stereochemically favourable hydrogen bonds. However, the incorporation of guanidino groups into a polymeric structure and the therapeutic application of guanidino groups and polymeric structures containing guanidino groups has not been suggested previously.

Accordingly the present invention provides a physiologically acceptable polymer comprising a backbone to which are directly or indirectly attached guanidino groups, the polymer having a minimum molecular weight of 10,000.

The present invention extends to the use of the polymeric compounds of the invention in therapy, for example in pharmaceutical compositions and foodstuffs as described hereinafter. The invention is of particular interest for the treatment of kidney patients for the control of phosphate uptake from the diet and the removal of excess phosphate from the blood of such individuals.

The polymeric material to which the guanidino groups are attached can essentially be of any polymeric structure, since the nature of the polymeric backbone is not of primary importance in phosphate binding, this effect being due rather to the presence in the polymer of the guanidino groups. However, preferably the polymer is pharmaceutically acceptable and of such appropriate molecular weight as to be not absorbed by patients when taken orally, but to remain in the intestine. The molecular weight of the guanidino group-containing polymer is at least 10,000.

The guanidino group-containing polymers of the invention must be physiologically acceptable. As is known to persons skilled in the art, polymers are large molecules made up of small simple chemical units. In some cases the repetition is linear and a chain is built up of these units. In other cases the chains are branched or interconnected to form 3-dimensional networks. Such 3-dimensional networks can also be formed by cross-linking polymer chains. Types of polymer which may be used include those having an organic backbone, particularly polymers in which the backbone consists of carbon atoms, for example polyvinyl alcohol derived polymers, polyacrylic and polymethacrylic acid derived polymers, and other polvinyl, polyisobutylene and polyisoprene polymers, but also polymers in which the organic backbone includes hetero atoms such as oxygen or nitrogen together with the carbon atoms. Polymers of particular interest in the current invention include polymers forming a 3-dimensional network structure for example as a result of further cross-linking the polymer. The degree of cross-linking controls the porosity of the polymeric matrix which in turn can influence both the binding capacity and the molecular weight selectivity of the matrix. Preferred polymers of this type include polymers having a polyethylene backbone cross-linked with divinyl benzene. Also of some interest are polymers having an inorganic backbone, for example the polyphosphazene polymers. The polymers may be copolymers derived from two or more different types of monomer. Since the preferred route of administration is orally and they remain in the intestine and are not absorbed into the patient's bloodstream, the polymers of the invention are even more preferably palatable to the consumer. Examples of such polymers are carbohydrate polymers including cellulose and agarose.

The carbohydrate polymers are particularly advantageous since many kidney patients take carbohydrate to bulk up their diet. Hence in this way one is providing dietary bulk whilst at the same time preventing phosphate absorption from the diet and effecting its excretion via the faeces and not via the bloodstream and kidneys, and thus reducing undesirable toxic effects.

The guanidino groups are attached to the polymer backbone by means of chemical bonding through the terminal NH group of the guanidino group (NH$_2$—C(=NH)—NH—). The chemical bonding of the guanidino groups to the polymer backbone may be directly or via some form of grouping acting as a "spacer" through which it is attached to the polymer backbone. Various forms of attachment may be used, preferred forms varying according to the basic type of polymer. For example, alkylene groups of 1–4 carbon atoms, amide groups, ether groups or a combination thereof may be used. The preferred mode of attachment of guanidino groups to the polymer backbone will obviously depend upon the nature of the backbone but for simplicity direct bonding between atoms of the backbone and the NH group of the guanidino group is preferred where possible.

The amount of polymer to be administered to the patient is an important consideration bearing upon the number of guanidino groups present in the polymer. Preferably the proportion of guanidino groups to the rest of the polymer is in a range between 1 part by weight of guanidino groups to 1 part by weight of the rest of the polymer and 1 part by weight of guanidino groups to 100 parts by weight of the rest of the polymer. Preferably the range is between 1 part by weight of guanidino groups to 1 part by weight of the rest of the polymer and 1 part by weight of guanidino groups to 10 parts by weight of the rest of the polymer, for example 1 part to 10 parts.

Methods of preparing the guanidino-containing polymers will be apparent to a person skilled in the art but for example, they may be prepared following the teachings of Schnaar, R. L. and Lee, Y. C., 1975, Biochemistry 14, 1535–1541 who describes a method for linking biologicaly active ligands to a polymer matrix, or the polymers may also conveniently be prepared through the reaction with a polymer containing amino groups attached to the polymer backbone of (a) 3,5-dimethylpyrazole-1-carboxamidine nitrate, (b) S-methylthiouronium sulphate or (c) O-methylpseudourea hydrogen sulphate.

It has been found that the polymers of the invention are able specifically to bind phosphate anions in vitro and in vivo. The polymers of the invention thus have a particular use for the prevention of phosphate uptake from the diet and also the removal of excess phosphate from the blood of those patients with deficient kidneys since the binding of phosphate in the intestine from the diet disturbs the body equilibrium and effects movement of phosphate from the bloodstream into the intestine. The polymers of the invention may be administered to the patients orally either as foodstuff or as an addition to a foodstuff, or as a pharmaceutical composition.

According to a second aspect of the invention there is provided a foodstuff or an addition to a foodstuff comprising a physiologically acceptable polymer of the invention. Such foodstuffs may take a variety of forms, for example taking the form of conventional human food.

According to a third aspect of the invention there is provided a pharmaceutical composition adapted for oral administration comprising a physiologically acceptable polymer of the invention in association with a pharmaceutically acceptable diluent or carrier.

The guanidino group-containing polymer may be formulated in a pharmaceutical composition by a variety of methods. The pharmaceutical composition will normally be orally administered since it should be present in the intestine of the patient rather than in the bloodstream. Although compositions incorporating a liquid diluent may be used for oral administration, it is more preferable to use compositions incorporating a solid carrier material such as starch, lactose, dextrin or magnesium stearate. Such solid compositions may conveniently be of a formed type, for example as tablets, capsules, etc.

The pharmaceutical compositions, foodstuffs or addition for foodstuffs may be formulated in unit dosage form, i.e. in the form of discrete portions containing a unit dose, or a multiple or sub-unit of a unit dose. The dosage of the guanidino group-containing polymer will of course depend upon individual circumstances, and the severity of kidney disease in the patient, as well as the chemical structure of the guanidino group-containing polymer. By way of guidance a daily dosage in terms of guanidine would be in the range 1 g to 10 g and thus the amount of polymer can be calculated accordingly.

According to a further aspect of the invention there is provided a method of treatment of a patient which comprises administering to said patient a guanidino group-containing polymer described hereinbefore in order to control phosphate uptake from the diet and to remove excess phosphate from the bloodstream.

According to a further aspect of the invention there is provided the use of a guanidino-containing polymer described hereinbefore for the manufacture of a medicament for the treatment of a patient in order to control phosphate uptake from the diet and to remove excess phosphate from the bloodstream.

BRIEF DESCRIPTION OF THE DRAWINGS

The invention will now be illustrated by way of Example only with reference to the accompanying Drawing in which FIGS. 1(a) and 1(b) show the effect of a diet incorporating a guanidino group-containing polymer on the levels of serum phosphate and bicarbonate in normal rats.

EXAMPLES

Example 1

PREPARATION OF GUANIDINO GROUP-CONTAINING POLYVINYL-BASED RESINS

An aminated resin is reacted in methanol under reflux with an excess of (a) 3,5-dimethylpyrazole-1-carboxamidine nitrate, (b) S-methylisothiouronium sulphate or (c) O-methylpseudourea hydrogen sulphate to convert the amino groups attached to the polymer backbone into guanidino groups. The extent of reaction may be followed through testing for the by-product produced so that with reagent (a) it may be monitored by extraction with ether to determine the amount of 3,5-dimethylpyrazole formed. The resin is purified by washing sequentially with methanol and water until the eluate is free from inorganic ions.

Resin starting materials (A) A commercially available poly(acrylonitrile) resin was reduced with an excess of lithium aluminium hydride in ether or tetrahydrofuran under reflux or alternatively by catalytic hydrogenation over $PtO_2$ (60 psi, 20° C.) in glacial acetic acid containing sulphuric acid. The resulting aminated resin was purified by successive washings with dilute aqueous hydrochloric acid and then water until the eluates are free from chloride ions and inorganic cations. The $Cl^-$ form of the resin was converted to the free base form by treatment with 1M aqueous sodium hydroxide followed by washing with water.

(B) A commercially available poly(chloromethylstyrene) resin was treated with an excess of saturated methanolic ammonia solution at 20° C. for 48 hours followed by thorough washing with water until the eluate was free from ammonia.

Example 2

IN VITRO STUDIES DETERMINATION OF PHOSPHATE BINDING CAPACITY OF DIFFERENT GUANINIDINO GROUP-CONTAINING POLYVINYL-BASED RESINS

The following three resins were compared. (Amberlite is a Registered Trade Mark).

A poly(styrylmethylguanidinium) chloride resin prepared as in Example 1 (B).

A poly(allylguanidinium) chloride resin prepared as in Example 1 (A).

Amberlite 1R410 ($Cl^-$) as a control material.

The theoretical binding capacity of the above polymers was determined by elemental analysis. The actual binding capacity of the resins was determined by ion-exchange chromatography using $^{32}P$-labelled phosphate. The columns were prepared from 5 g of dry resin. Binding experiments were conducted at pH 7.4, both in the absence and presence of competing chloride anions. The concentrations of phosphate and chloride were 10 and 150 mM respectively. The results are presented in Table 1.

TABLE 1

|  | | Phosphate Binding Capacity (mEq $g^{-1}$) | |
| --- | --- | --- | --- |
|  | Theoretical | In absence of chloride | In presence of chloride |
| poly(styrylmethyl-guanidinium) chloride | 3.8 | 1.02 | 0.47 |
| poly(allylguanidinium) chloride | 2.3 | — | 1.41 |
| Amberlite IR410 ($Cl^-$) | 4.9 | — | 0.26 |

Although the poly(allylguanidinium) chloride resin has a lower binding capacity as judged by binding functions, a greater proportion is bioavailable as judged by the binding of $^{32}P$-phosphate. Chloride does compete with phosphate for the binding site of polyguanidine resins, but it does so with low efficiency. Thus even when chloride was present to a 15 molar excess, phosphate binding was only reduced by 50%. It has also been demonstrated that the poly (allylguanidinium) chloride resin was selective for phosphate in the presence of 150 molar excess of chloride. Amberlite IR410 ($Cl^-$) also bound phosphate, but less efficently than the new polyguanidine resins.

Example 3

IN VIVO STUDIES ABILITY OF A GUANIDINO GROUP-CONTAINING POLYVINYL-BASED RESIN TO LOWER SERUM PHOSPHATE LEVELS IN RATS

Experimental Protocol

The polyvinyl-based resin used was a poly (allylguanidinium) chloride resin prepared as in Example 1 which is identified hereinafter as the PVG resin. This resin comprised a polyethylene backbone cross-linked by divinyl benzene. This backbone was highly substituted by 2-guanidino methyl groups.

The study was carried out in two stages:

A) Efficacy of the resin binder in normal rats

Six rats (original strain: Wistar, male, 145–160 g) were bled via the tail (0.5 ml) and fed for 7 days with (powdered) rat chow (CRM diet, SDS, Essex) mixed with powdered PVG-matrix (0.5 g resin/15 g diet). Rats were given 15 g diet daily. Thereafter, the animals were bled as above, and the serum analysed for urea, creatinine and electrolytes.

B) Efficacy of the resin binder in chronic renal failure

Chronic renal failure was induced in a group of 11 male, Wistar rats (wt=160–190 g) by performing a sub-total nephrectomy (NX) in two stages: the upper and lower poles of the left kidney were removed, followed after 9–10 days by a total right nephrectomy. The control group (n=6) included rats in which sham operations (SO) had been performed.

A week after the second operation both the sham-operated and nephrectomised rats were bled (about 0.5 ml via tail-tip clipping). One group (n=3 SO; n=6 NX) was then given, for 1 week, powdered rat diet+resin (31 g/rat/day; 0.5 g resin/15 g diet). The other group (n=3 SO; n=5 NX) received for 7 days powdered rat chow (31 g/rat/day) followed for a further week by rat chow+resin. Rats were bled at the completion of each stage. All serum samples were then analysed for urea, creatinine and electrolytes. Bleeding of rats was performed at roughly the same time of the day to minimise any possibility of diurnal variation. The haemoglobin data for the rats used in this study was SO group (n=5)=17.52±1.83 g/dl NX group (n=11)=15.32±3.02 g/dl Results A Efficacy of resin binder in normal rats Rats were found to eat all the PVG-containing diet provided on a daily basis. The gain in body weight over the week ranged from 7–18 g. Initial serum phosphate levels were markedly higher than in man (3.81±0.33(6) mmol/l, mean±SD), and fell in all cases following feeding of rat chow containing PVG (FIG. 1, which shows the plots for serum phosphate and bicarbonate levels in the individual rats). The mean percentage decrease in phosphate was 15.9% (±5.3, SD). A comparable decrease in serum bicarbonate (19.7±17.2% (6)) was also evident on the PVG-diet. Serum calcium levels showed no consistent changes.

The data demonstrate that the PVG resin has the capacity to lower phosphate levels.

B) Efficacy of resin binder in chronic renal failure

Sub-total nephrectomy resulted in the onset of chronic renal failure (CRF), as reflected by significant increases in the serum creatinine and urea levels and by a fall in the haemoglobin content (Table 2). The calcium levels, though somewhat elevated in the NX group, failed to reach statistical significance (p=0.052). Phosphate levels in contrast showed no significant alterations following sub-total nephrectomy (Table 2).

TABLE 2

Comparison of Various Biochemical Parameters in Sham-Operated (SO) and Nephrectomised (NX) Rats

| Parameter | SO | NX | p |
|---|---|---|---|
| Creatinine ($\mu$M) | 51.0 ± 2.1 | 78.9 ± 7.6 | <0.001 |
| Urea (mM) | 5.9 ± 1.0 | 13.2 ± 1.5 | <0.001 |
| Haemoglobin (g/dl) | 17.5 ± 1.8 | 15.3 ± 3.0 | <0.05 |
| Na$^+$ (mM) | 142 ± 1 | 43.2 ± 5 | >0.05 |
| K$^+$ (mM) | 5.8 ± 0.5 | 6.0 ± 0.3 | >0.05 |
| Ca (mM) | 2.58 ± 0.08 | 2.72 ± 0.15 | >0.05 |
| Phosphate (mM) | 3.49 ± 0.18 | 3.37 ± 0.31 | >0.05 |

Results: mean ± SD for (n) animals. N = 6 and 11 for the SO and NX groups, respectively.

The group of NX rats fed PVG-diet were seen to have somewhat improved renal function as reflected by a significant decrease in urea (p=0.013) and a small drop in the creatinine levels (Table 3). Serum phosphate levels were also marginally reduced (3.37±0.26(6) to 3.18±0.24, p>0.05). Similarly, the SO group initially fed the PVG-diet showed a significant decrease in the phosphate level (3.58±0.1(3) to 3.38±0.04, p<0.04), whilst the other parameters remained unchanged.

TABLE 3

| | Sham-operated (n = 3) | | Nephrectomised (n = 4) | |
|---|---|---|---|---|
| Group Parameter | Initial | After PVG- for 1 wk | Initial | After PVG- for 1 wk |
| Na$^+$ (mM) | 142.3 ± 1.15 | 142.7 ± 1.16 | 144.2 ± 5.85 | 142.3 ± 2.58 |
| K$^+$ (mM) | 5.6 ± 0.35 | 5.87 ± 0.42 | 6.03 ± 0.19* | 5.98 ± 0.57 |
| Urea (mM) | 5.13 ± 0.49 | 5.23 ± 0.15 | 13.25 ± 0.99** | 11.77 ± 0.69++ |
| Creatinine ($\mu$M) | 52.0 ± 2.00 | 53.67 ± 2.52 | 77.33 ± 6.59** | 76.17 ± 4.07 |
| Ca$^{2+}$ (mM) | 2.53 ± 0.095 | 2.62 ± 0.09 | 2.73 ± 0.20 | 2.76 ± 0.085 |
| PO$_4^3$ (mM) | 3.58 ± 0.01 | 3.38 ± 0.04$^+$ | 3.37 ± 0.26 | 3.18 ± 0.24 |

Data: mean ± SD
Stats: * p < 0.05; ** p <0.001 as compared to SO group + p < 0.05; ++ p <0.02 as compared to initial values.

The NX group, initially given the normal diet, showed insignificant changes in urea, phosphate, creatinine and calcium levels (Table 4). The SO group showed a very similar pattern of changes. On changing to the PVG diet, the urea, creatinine and calcium levels showed reductions (p>0.05 in all cases). Serum phosphate fell in the SO group (3.27±0.5(3) to 2.80±0.08(3), p>0.05), but remained unchanged in the NX group (3.11±0.15(5) vs 3.27±0.35).

The 2-step surgical procedure resulted in the onset of CRF as reflected by increases in urea and creatinine and by a fall in haemoglobin. However, the rats were found to eat well and to put on weight (comparable increases in both groups). Calcium levels in the NX group were slightly raised, whilst phosphate levels

TABLE 4

| | Sham-operated (n = 3) | | | Nephrectoinised (n = 5) | | |
|---|---|---|---|---|---|---|
| Group Parameter | Initial | Diet − PVG for 1 wk | Diet + PVG for 1 wk | Initial | Diet − PVG for 1 wk | Diet + PVG for 1 wk |
| Na$^+$ (mM) | 141.7 ± 0.58 | 142.0 ± 0 | 141.3 ± 0.58 | 142.0 ± 2.00 | 143.4 ± 2.07 | 141.2 ± 0.45 |
| K$^+$ (mM) | 6.0 ± 0.56 | 5.93 ± 0.67 | 5.4 ± 0.52 | 5.86 ± 0.47 | 6.02 ± 0.13 | 5.96 ± 0.54 |
| Urea (mM) | 6.57 ± 0.75 | 6.7 ± 0.36 | 5.97 ± 0.32 | 13.16 ± 2.04 | 13.76 ± 2.53 | 11.82 ± 1.41 |
| Creatinine ($\mu$M) | 50.0 ± 2.00 | 57.7 ± 2.08** | 56.7 ± 5.69 | 80.8 ± 9.09 | 86.2 ± 9.2 | 81.4 ± 6.43 |
| Ca$^{2+}$ (mM) | 2.63 ± 0.03 | 2.68 ± 0.1 | 2.57 ± 0.02 | 2.71 ± 0.06 | 2.78 ± 0.08 | 2.67 ± 0.09 |
| PO$_4^{3-}$ (mM) | 3.41 ± 0.21 | 3.27 ± 0.5 | 2.8 ± 0.08 | 3.36 ± 0.39 | 3.11 ± 0.15 | 3.27 ± 0.35 |

Data: mean ± SD
Stats: * p < 0.05; ** p < 0.01 as compared to initial SO values + p < 0.002 as compared to SO group remained unaltered. The absence of a rise in serum phosphate in the NX group may be due to the fact that the starting (initial) values are high (>3 mmol/l), the mild degree of renal failure, a low dietary phosphate intake, the rats were actively growing and accumulating phosphate in bone, etc., or a species difference in response to nephrectomy.

Phosphate levels decreased following the introduction of the PVG diet in both control and nephrectomised animals. There was surprisingly evidence of improvement in renal function following feeding of rats with PVG-diet (refer to urea and creatinine values, Tables 3 and 4).

Example 4

CHEMICAL ANALYSIS OF POLYVINYL GUANIDINO PVG RESIN

The polymeric resin tested comprised a polyethylene backbone cross-linked by divinyl benzene. This backbone was highly substituted by 2-guanidino methyl groups. This is the PVG resin referred to in previous Examples.

(A) Analysis of Resin Capacity—This was determined by
  (i) elemental analysis and
  (ii) binding of $^{32}$p at pH 8.0
(I) Elemental Analysis Equilibration of resin with HCl (1M) and subsequent washing with distilled water and drying to constant weight yielded the following analyses:

|   | (a) | (b) |
|---|---|---|
| C | 43.12 | 44.60 |
| H | 7.37 | 7.5 |
| N | 20.20 | 20.10 |
| Cl | 10.60 | 10.15 |
| P | 0 | 0 |

This corresponds to a binding capacity of 5.3 mEq Cl⁻ per gram of dry resin.

Equilibration of resin with $H_3PO_4$ (1M) and subsequent washing with distilled water and drying to constant weight yielded the following analyses:

|   | (a) | (b) |
|---|---|---|
| C | 37.6 | 35.9 |
| H | 7.1 | 6.8 |
| N | 16.5 | 16.1 |
| Cl | 0.2 | 0.7 |
| P | 9.2 | 9.3 |
| ($PO_4$) | 27.6 | 27.6 |

This corresponds to a binding capacity of 2.88 mEq phosphate per gram of dry resin. Thus, the capacity of the polymer for both chloride and phosphate anions is high and compares favourably with other Dowex resins.

$^{32}$P-phosphate

Resin (400 mg) was added to a narrow column containing a fine sintered glass filter. The flow rate of fluid through the column was adjusted to 1 ml min$^{-1}$ by a peristaltic pump. The resin was washed successively with NaOH (1M, 10 ml) $H_2O$ (20 ml), HCl (1M, 10 ml) and $H_2O$ (20 ml). In this state the column was completely charged with Cl⁻ anions.

The column was then eluted with $^{32}$-phosphate (100 mM, pH 8.0) in 1.0 ml portions, recording the percentage of phosphate binding with each addition. The date are presented in Table 5.

TABLE 5

Phosphate binding capacity of resin (pH 8.0)

| Fraction # | Percentage of phosphate bound (%) | Amount of phosphate bound meq g$^{-1}$ |
|---|---|---|
| 1 | 98.4 | 0.246 |
| 2 | 95.9 | 0.240 |
| 3 | 93.7 | 0.234 |
| 4 | 85.3 | 0.213 |
| 5 | 75.0 | 0.188 |

TABLE 5-continued

Phosphate binding capacity of resin (pH 8.0)

| Fraction # | Percentage of phosphate bound (%) | Amount of phosphate bound meq g$^{-1}$ |
|---|---|---|
| 6 | 55.1 | 0.137 |
| 7 | 31.5 | 0.079 |
| 8 | 14.2 | 0.036 |
| 9 | 0.0 | 0.00 |
| Total |  | 1.37 |

Each aliquot added to the column was 1 ml of $Na_2HPO_4$ (pH 8.0, 100 mM). Thus, at pH 8.0 the phosphate capacity was somewhat reduced to 1.37 mEq g$^{-1}$ resin. This was 50% of value obtained when phosphoric acid was used to equilibrate the column at pH 1.0. This difference possibly relates to the ionic state of phosphate at the two pH values.

(B) Competition between anions for polymer binding sites

Two experimental procedures were adopted: one, competition in the absence of added phosphate and the second, competition in the presence of phosphate (1 mM).

Competition in absence of phosphate

Competition with the following anions was investigated:

chloride bicarbonate sulphate taurocholate glycocholate

The column (400 mg resin) was loaded with $^{32}$P-phosphate to greater 80% capacity and then equilibrated with Tris.HCl (pH 8.0, 5 mM). The column was then eluted with various competing anions in 50 ml aliquots of Tris.HCl (pH 8.0, 5 mM). The results are shown in Table 6.

TABLE 6

Displacement of phosphate from resin by various anions at pH 8.0

| Fraction # | NaCl (10 mM) | NaCl (25 mM) | $Na_2SO_4$ (10 mM) | $NaHCO_3$ (10 mM) | Na taurocholate (10 mM) | Na glycocholate (10 mM) |
|---|---|---|---|---|---|---|
| 1 | 8.8 | 14.4 | 32.4 | 11.0 | 1.9 | 2.1 |
| 2 | 6.5 | 9.3 | 31.3 | 11.6 | 0.7 | 1.0 |
| 3 | 5.6 | 7.2 | 22.1 | 14.3 | 1.0 | 1.4 |
| Total | 20.9% | 30.9 | 85.8 | 36.9 | 3.6 | 4.5 |

Each fraction consisted of 50 ml of column effluent. Column buffered to pH 8.0 throughout study.

Table 6 shows that sulphate was the only anion which demonstrated efficient displacement activity. This is probably because $SO_4^{2-}$ can interact with guanidino functions in a similar manner to that of phosphate. The monobasic anions Cl⁻ and $HCO_3^-$ are much less efficient at displacing phosphate anions. If large volumes of fluid are used then at high concentration, Cl⁻ will eventually displace the phosphate anion. This is shown below in Table 7. Anionic bile salts are extremely inefficient at displacing phosphate, implying that they have only a very low affinity for the resin. It is likely that they are unable to penetrate the resin matrix.

TABLE 7

Displacement of phosphate from resin by chloride at pH 8.0

| Fraction # | [NaCl] mM | Percentage of Phosphate displaced |
|---|---|---|
| 1 | 5 | 9 |
| 2 | 10 | 10.3 |
| 3 | 50 | 23 |
| 4 | 100 | 19 |
| 5 | 100 | 10.9 |
| 6 | 100 | 6.6 |
| Total Displacement | | 78.8% |

Each fraction consisted of 50 ml of column effluent.
Competition in presence of phosphate In this investigation the column was eluted with Tris HCl (pH 8.0, 5 mM) containing $Na_2HPO_4$ (1 mM) of identical specific radioactivity to the phosphate used to load the resin column. Under such conditions if phosphate displaces phosphate, the radioactivity on the column will remain unchanged. Under these conditions chloride does displace phosphate but only with low efficiency. This is shown in Table 8 below. Thus, no detectable phosphate was displaced in the presence of 10 mM NaCl,; however, it began to be displaced at 50 mM and higher concentrations of NaCl.

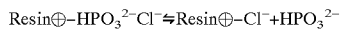

$$\text{Resin}\oplus\text{-HPO}_3{}^{2-}\text{Cl}^-\rightleftharpoons\text{Resin}\oplus\text{-Cl}^-+\text{HPO}_3{}^{2-}$$

All the reported experiments were repeated on at least two independent occasions.

TABLE 8

Displacement of phosphate from resin by chloride in presence of phosphate (1 mM) pH 8.0

| Fraction # | [NaCl] mM | Percentage of Phosphate eluted |
|---|---|---|
| 1 | 5 | 0 |
| 2 | 5 | 0 |
| 3 | 5 | 0 |
| 4 | 10 | 0 |
| 5 | 50 | 16% |
| 6 | 100 | 19% |

Each fraction eluted from the column=50 ml.
Conclusions

The guanidino-containing resin utilised in this preliminary investigation is remarkably selective for phosphate anions. Monobasic anions and bile salts only displace phosphate slowly. When studied in the presence of phosphate (1 mM), only high concentrations of NaCl (50–100 mM) cause appreciable displacement of the phosphate (e.g. <20% after 1 h incubation with 100 mM NaCl). Sulphate, as expected, is a good competitor for bound phosphate but unlike chloride, this anion is likely to be at quite low levels in the lumen of the gastrointestinal tract, certainly lower than those of orthophosphate.

What is claimed is:

1. A method of treatment of a patient in need of the prevention of phosphate uptake from the diet or removal of excess phosphate from the blood, which comprises administering to said patient an amount effective to control phosphate uptake from the diet or to remove excess phosphate from the blood, respectively, of a physiologically acceptable polymer comprising a backbone to which are attached guanidino groups chemically bonded thereto through the terminal NH groups of said guanidino groups, said polymer having a minimum molecular weight of 10,000.

2. A method of treatment of a patient in need of the prevention of phosphate uptake from the diet or removal of excess phosphate from the blood, which comprises administering to said patient an amount effective to control phosphate uptake from the diet or to remove excess phosphate from the blood, respectively, of a physiologically acceptable polymer comprising a backbone to which are attached guanidino groups chemically bonded thereto through the terminal NH groups of said guanidino groups, said polymer having a minimum molecular weight of 10,000 having a 3-dimensional network in which backbone polymer chains are cross-linked.

3. The method of claim 1 wherein the polymer has a backbone is derived from a polyvinyl polymer.

4. The method of claim 2 wherein the polymer has a backbone derived from a polyvinyl polymer.

5. The method of claim 2 wherein the polymer has a polyethylene backbone cross-linked by divinyl benzene.

6. The method of claim 1 wherein the polymer is a polystyrene to which are attached guanidino groups.

7. The method of claim 1 wherein the polymer is a guanidinomethylpolystyrene.

8. The method of claim 2 wherein the cross-linked polymer is a cross-linked guanidinomethylpolystyrene.

9. The method of claim 1 wherein the polymer is a methanol-washable and water-washable poly(styrylmethyl-guanidinium)chloride.

10. The method of claim 1 wherein the proportion of guanidino groups in the polymer is in a range between 1 part by weight of guanidino groups to I part by weight of the rest of the polymer and 1 part by weight of guanidino groups to 100 parts by weight of the rest of the polymer.

11. The method of claim 1 wherein the range is between 1 part by weight of guanidino groups to 1 part by weight of the rest of the polymer and 1 part by weight of guanidino groups to 10 parts by weight of the rest of the polymer.

12. The method of claim 1 wherein the guanidino groups are indirectly attached to the polymer backbone via a spacer.

13. The method of claim 10 wherein the spacer is an alkylene group of 1–4 carbon atoms.

14. The method of claim 2 wherein the guanidino groups are indirectly attached to the polymer backbone via an alkylene group of 1–4 carbon atoms.

15. The method of claim 1 wherein the polymer is administered to the patient orally, in association with a pharmaceutically acceptable diluent or carrier adapted for oral administration.

16. The method of claim 2 wherein the polymer is administered to the patient orally, in association with a pharmaceutically acceptable diluent or carrier adapted for oral administration.

17. The method of claim 16 wherein the carrier is a solid.

18. The method of claim 17 wherein the carrier is a capsule containing the polymer.

19. The method of claim 16 wherein the polymer is administered to the patient in the form of a foodstuff.

20. The method of claim 1 wherein the patient is suffering from a kidney disorder.

21. The method of claim 2 wherein the patient is suffering from a kidney disorder.

* * * * *